United States Patent [19]

Peck

[11] 4,393,078
[45] Jul. 12, 1983

[54] BUPROPION AND ETHANOL

[75] Inventor: Anthony W. Peck, Bromley, England

[73] Assignee: Burroughs Wellcome Co., Research Triangle Park, N.C.

[21] Appl. No.: 358,354

[22] Filed: Mar. 15, 1982

[51] Int. Cl.³ .......................................... A61K 31/135
[52] U.S. Cl. .................................................... 424/330
[58] Field of Search ......................................... 424/330

[56] References Cited

U.S. PATENT DOCUMENTS 3,819,706  6/1974  Mehta ................................. 424/330
3,885,046  5/1975  Mehta ................................. 424/330

Primary Examiner—Stanley J. Friedman

[57] ABSTRACT

This invention relates a method of restoring slowed mental ability in humans caused by ethanol by treatment with the compound of formula I

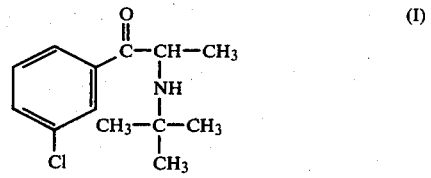

or a pharmaceutically acceptable acid addition salt thereof in a non-toxic, effective therapeutic amount to a human in need thereof.

9 Claims, No Drawings

BUPROPION AND ETHANOL

Since ancient times poor coordination and mental impairment have been associated with the consumption by humans of ethanol which is also known as ethyl alcohol, grain alcohol or more commonly "alcohol" (the terms "ethanol" and "alcohol" are used interchangeably herein). Equally associated throughout history has been the detrimental social and economic impact of these effects. In more present times such altered human mental and physical states are dramatically and tragically demonstrated by the alarming number of accidents and violent crimes involving persons under the influence of alcohol.

The compound of formula I

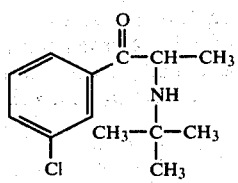

(named m-chloro-α-t-butylaminopropiophenone) commonly known as bupropion and salts thereof were disclosed as being antidepressants in U.S. Pat. Nos. 3,819,706 and 3,885,046. It has now been found surprisingly that this compound when administered to a human intoxicated with ethanol significantly restores impaired mental ability.

The amount of bupropion required to substantially reverse the mental functional impairment depends on a number of factors such as the concentration of ethanol in the blood, weight and metabolism rate of the person receiving treatment and the presence of other drugs in the blood of the treated person which may interact with bupropion and/or ethanol. However, for an adult of approximately 70 kg who has consumed 16 to 32 mL of ethanol within 10 minutes and who has not taken any other drug within the past 24 hours the effective dose of bupropion will generally lie in the range of 50 mg to 300 mg and preferably from 75 mg to 200 mg.

Bupropion or the pharmaceutically acceptable acid addition salt thereof is preferably administered in unit dosage form to the human being treated.

A pharmaceutical composition containing bupropion or a pharmaceutically acceptable salt thereof, may be presented in discrete units as tablets, capsules, ampules or suppositories, each containing an effective amount of the compound salt for treatment of ethanol induced mental impairment. A compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned ingredients, the pharmaceutical composition of this invention may include one or more of additional ingredients e.g., pharmaceutically acceptable carriers such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

The compound used in this invention is preferably presented for use as a pharmaceutically acceptable acid addition salt. Examples of some of the pharmaceutically acceptable salts which can be utilized are salts of the following acids: hydrochloric, sulfuric, phosphoric and toluenesulphonic.

Reference should be had to U.S. Pat. Nos. 3,819,706 and 3,885,046, which are incorporated herein by reference hereto for a description of the preparation of the compound of formula (I), acid addition salts thereof, tablets, capsules, parenteral solutions and suppositories incorporating same.

EXAMPLE 1

Administration of Bupropion to humans after inducing mental impairment with ethanol The effects of treatments as follows:
Bupropion placebo + alcohol "placebo"
Bupropion HCl 100 mg + alcohol "placebo"
Bupropion placebo + alcohol 16 mL
Bupropion placebo + alcohol 32 mL
Bupropion HCl 100 mg + alcohol 16 mL
Bupropion HCl 100 mg + alcohol 32 mL
were separately examined in twelve healthy volunteers (6 males and 6 females) using a balanced cross over design and double blind conditions. Results were evaluated by analysis of variance and values of $p < 0.05$ taken as significant.

Bupropion placebo and bupropion were prepared as tablets (100 mg size) identical in appearance. Alcohol and alcohol placebo solutions were prepared as an orange flavoured, iced drink to a total volume of 200 mL. One mL rum was applied to the rim of the glass just before consumption to confuse the subjects as to the amount of alcohol they were receiving.

The twelve subjects received all six treatments at weekly intervals according to two 6×6 Latin square designs which were balanced for occasion, treatment, and preceding treatment. Subjects were studied in groups of four on each experimental day. Each group comprised the same four people on each occasion and was always studied on the same day of the week.

Using the Wilkinson auditory vigilance test (*Prog. Clin. Psychol.*, 8, 28-43 (1968)), no active treatment or combination of treatments produced any change significantly different from placebo. However, alcohol 32 ml alone significantly reduced the number of signals detected when compared with bupropion 100 mg alone and in combination with 16 and 32 mL of alcohol. No significant changes in reaction time or short-term memory occurred.

Visual analogue scales (Lader and Norris, *Psychopharmacologia (Berl.)*, 16, 115 (1969)) indicated that the subjects were mentally slower after alcohol (32 mL) than after the alcohol placebo. Combination of bupropion (100 mg) with alcohol (32 mL) abolished this difference. A similar pattern occurred with group ratings indicating mental sedation.

Subjects were clearly able to differentiate between the low (16 mL) and high (32 mL) doses of alcohol when assessing their degree of inebriation. Combination of bupropion with alcohol made no difference to the ratings of inebriation.

The 32 mL dose of alcohol tended to increase energy in the low frequency (4-7.5 Hz) EEG bands, though this did not differ significantly from the placebo treatment. Combination of the 32 mL alcohol dose with bupropion, however, produced a significant reversal with lowered energy in the 4–7.5 Hz band.

I claim:

1. A method of reversing the impaired mental alertness effects of ethanol in a human, which comprises administering to a human who has consumed alcohol an effective, non-toxic amount of the compound of formula (I)

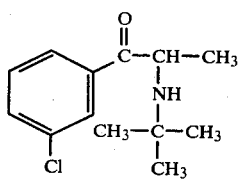
(I)

or a pharmaceutically acceptable acid addition salt thereof to reverse the mental alertness effects of ethanol in the human.

2. The method of claim 1 in which a pharmaceutically acceptable acid addition salt thereof is administered.

3. The method of claim 2 in which the salt is the hydrochloride salt.

4. The method of claim 1, 2 or 3 in which the compound or salt is administered in a pharmaceutically acceptable carrier therefor.

5. The method of claim 1, 2, 3 or 4 in which the compound or salt is administered orally.

6. The method of claim 5 in which the compound or salt is administered in a pharmaceutically acceptable carrier therefor.

7. The method of claim 1 in which the compound or salt is administered in a capsule or tablet containing a pharmaceutically acceptable carrier.

8. The method of claim 4 in which the pharmaceutically acceptable acid addition salt is administered.

9. The method of claim 5 in which the salt is hydrochloride.

* * * * *